(12) United States Patent
Rosani et al.

(10) Patent No.: US 9,776,824 B2
(45) Date of Patent: Oct. 3, 2017

(54) METHOD AND UNIT FOR FOLDING INCONTINENCE PADS

(75) Inventors: Marco Rosani, Vailate (IT); Gabriele Pastrello, Milan (IT); Luca Bugini, Fara Gera D'Adda (IT); Matteo Piantoni, Albino (IT); Alberto Perego, Milan (IT)

(73) Assignee: GDM S.p.A., Bologna (IT)

( * ) Notice: Subject to any disclaimer, the term of this patent is extended or adjusted under 35 U.S.C. 154(b) by 1121 days.

(21) Appl. No.: 13/991,109

(22) PCT Filed: Dec. 16, 2011

(86) PCT No.: PCT/IB2011/055731
§ 371 (c)(1),
(2), (4) Date: May 31, 2013

(87) PCT Pub. No.: WO2012/085790
PCT Pub. Date: Jun. 28, 2012

(65) Prior Publication Data
US 2013/0244853 A1    Sep. 19, 2013

(30) Foreign Application Priority Data
Dec. 23, 2010   (IT) .............................. BO2010A0756

(51) Int. Cl.
*B65H 45/00*   (2006.01)
*A61F 13/15*   (2006.01)
(Continued)

(52) U.S. Cl.
CPC ....... *B65H 45/00* (2013.01); *A61F 13/15747* (2013.01); *A61F 13/5514* (2013.01);
(Continued)

(58) Field of Classification Search
CPC .... B65H 45/00; B65H 45/12; B65H 2801/57; B65H 2701/177; A61F 13/15747; A61F 13/5514
(Continued)

(56) References Cited

U.S. PATENT DOCUMENTS 5,176,615 A    1/1993   Munsch
5,868,727 A *  2/1999   Barr ................. A61F 13/15707
                                                604/387
(Continued)

FOREIGN PATENT DOCUMENTS

EP    1424052       6/2004
EP    2154598 A2    2/2010
(Continued)

OTHER PUBLICATIONS

International Search Report and Written Opinion dated Feb. 22, 2012 for counterpart PCT application.

*Primary Examiner* — Thanh Truong
*Assistant Examiner* — Thomas Wittenschlaeger
(74) *Attorney, Agent, or Firm* — Shuttleworth & Ingersoll, PLC; Timothy J. Klima

(57) ABSTRACT

A method and unit for folding light incontinence pads having a substantially rectangular shape elongate according to a longitudinal axis and comprising a central absorbent pad and an outer edge, according to which a first end portion of the incontinence pad is folded on a central portion of the incontinence pad about a first fold line transversal to the longitudinal axis, a second end portion of the incontinence pad is folded on the first end portion about a second fold line transversal to the longitudinal axis, and elasticated segments of the edge located between the first and second fold lines are folded on the central portion; the step of folding the
(Continued)

elasticated segments of the edge being between a first sub-step of partly folding the first end portion and a second sub-step of completely folding the first end portion on the central portion.

7 Claims, 4 Drawing Sheets

(51) Int. Cl.
  *B65H 45/12* (2006.01)
  *A61F 13/551* (2006.01)
(52) U.S. Cl.
  CPC ....... *B65H 45/12* (2013.01); *B65H 2701/177* (2013.01); *B65H 2801/57* (2013.01)
(58) Field of Classification Search
  USPC .......................................................... 493/405
  See application file for complete search history.

(56) References Cited

U.S. PATENT DOCUMENTS

| 6,689,112 | B1 * | 2/2004 | Blanchard | A61F 13/476 |
| | | | | 604/385.04 |
| 2002/0177833 | A1 * | 11/2002 | Vangompel | A61F 13/4752 |
| | | | | 604/385.04 |
| 2011/0285887 | A1 | 11/2011 | Takenaka et al. | |

FOREIGN PATENT DOCUMENTS

| JP | 301329 | 11/1997 | |
| JP | WO 9825561 A1 * | 6/1998 | ......... A61F 13/5514 |
| JP | 2002177326 A | 6/2002 | |
| JP | 2009000567 A | 1/2009 | |
| JP | 4354103 | 10/2009 | |
| JP | 2010043237 A | 2/2010 | |
| JP | 2011244329 A | 12/2011 | |
| WO | WO 9820823 A2 * | 5/1998 | ....... A61F 13/15747 |
| WO | 2007070113 | 6/2007 | |

* cited by examiner

METHOD AND UNIT FOR FOLDING INCONTINENCE PADS

This application is the National Phase of International Application PCT/IB2011/055731 filed Dec. 16, 2011 which designated the U.S. and that International Application was published under PCT Article 21(2) in English.

This application claims priority to Italian Patent Application No. BO2010A000756 filed Dec. 23, 2010, which application is incorporated by reference herein.

TECHNICAL FIELD

This invention relates to a method and a unit for folding incontinence pads.

In particular, but without limiting the scope of the invention, this invention can be applied for folding feminine light incontinence pads.

BACKGROUND ART

As is known, incontinence pads of the above-mentioned type have a substantially rectangular shape and comprise two sheets, one impermeable, the other permeable, between which a section of absorbent padding material is interposed.

At the outline of the incontinence pad the two superposed sheets define a perimetric edge with a predetermined width.

The two longitudinal sides of the edge, at their central zone, have an elasticated segment.

As is known, machines for packaging incontinence pads of the above-mentioned type comprise a unit which folds them, about two fold lines which are transversal to their longitudinal axis, into three parts, respectively forming a front portion, a central portion and a rear portion of the incontinence pad.

Incontinence pads folded in this way into three superposed portions are then inserted individually or in groups in a wrapper by a further unit of the packaging machine.

It is also known that incontinence pads are required to have an anatomical shape.

That means that when the packaging of each incontinence pad is opened, the incontinence pad adopts a cup shape, in which the rear portion is angled, on the inner face side, towards the central and front portions, and in which the above-mentioned elasticated segments are angled towards each other, also on the side forming the inner face of the incontinence pad.

It should be noticed that the above-mentioned anatomical angles are difficult to obtain using prior art folding units.

Consequently, when the user opens the incontinence pad it is substantially flat or in any case angled in a way that is not anatomically satisfactory.

DISCLOSURE OF THE INVENTION

The aim of this invention is to provide a folding method and a folding unit which allow the obtainment of incontinence pads of the type described, which can adopt the above-mentioned anatomical shape after the folding operation and at the moment they are used.

The technical purpose indicated and the aims specified are substantially achieved by a method and a unit comprising the features described herein.

BRIEF DESCRIPTION OF THE DRAWINGS

Further features and advantages of this invention are more apparent in the non-limiting description which follows of a preferred, non-limiting embodiment of a method and a unit for folding incontinence pads, illustrated in the accompanying drawings, in which.

DETAILED DESCRIPTION OF THE PREFERRED EMBODIMENTS OF THE INVENTION

Figure 1:
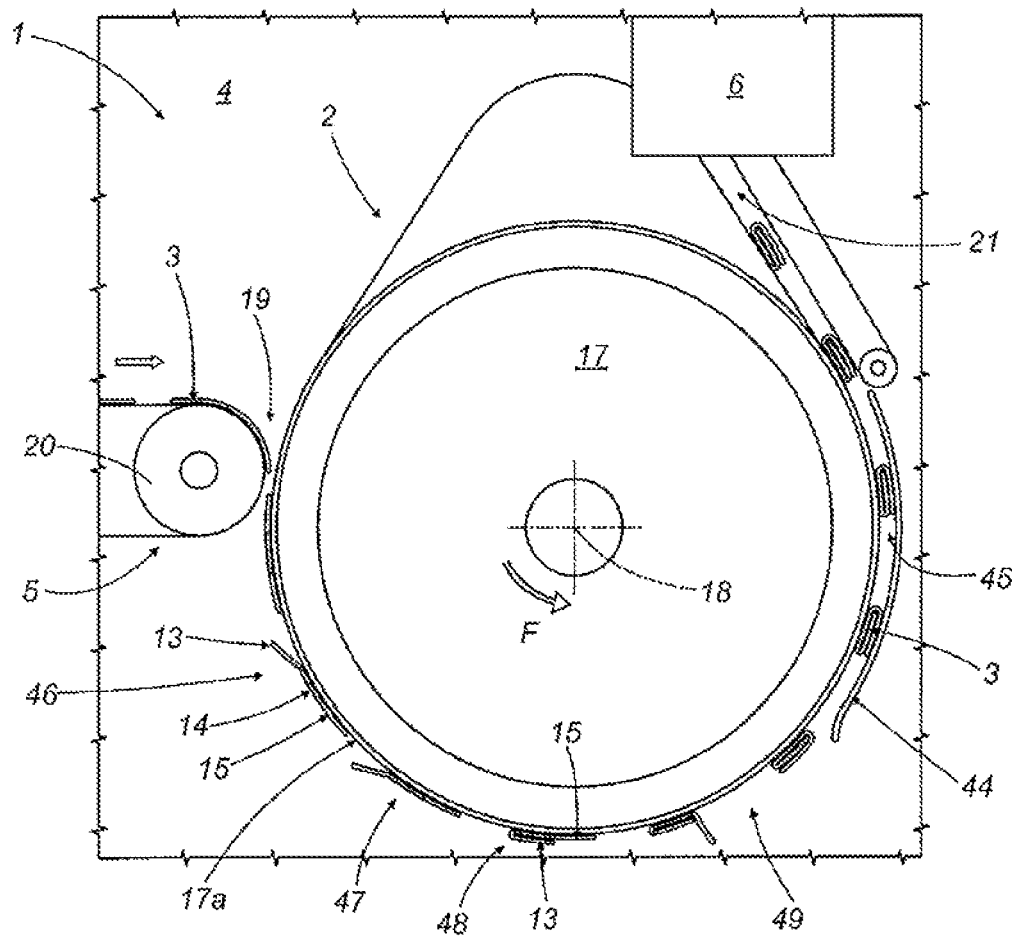
FIG. 1 is a schematic front view of a unit for folding incontinence pads according to this invention.

With reference to FIG. 1, the numeral 1 denotes a machine for packaging incontinence pads, comprising a unit 2 for folding incontinence pads 3, supported by a vertical wall 4.

The packaging machine 1 comprises a feed unit 5 and a user unit, schematically illustrated as a block 6, interposed between which there is the folding unit 2.

The incontinence pads 3 are, in particular, feminine light incontinence pads.

Figure 2:
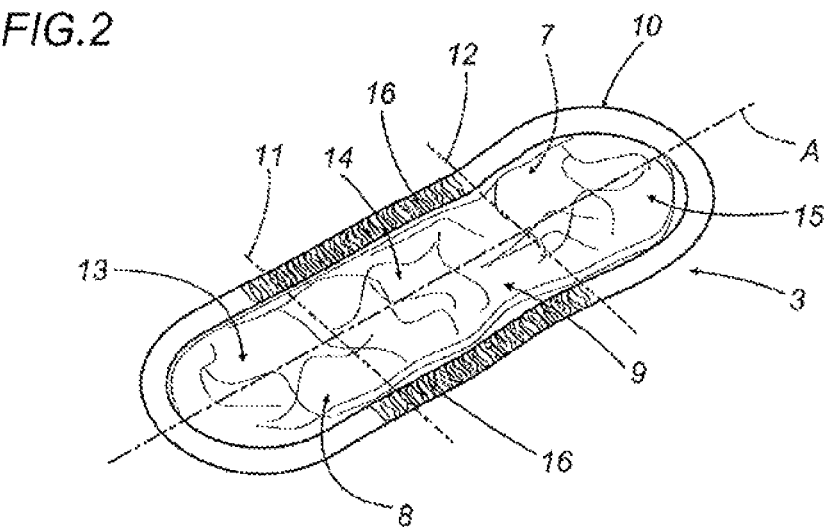
FIGS. 2 and 3 are perspective views of an incontinence pad processed by the unit of FIG. 1 in two different arrangements.
Figure 3:
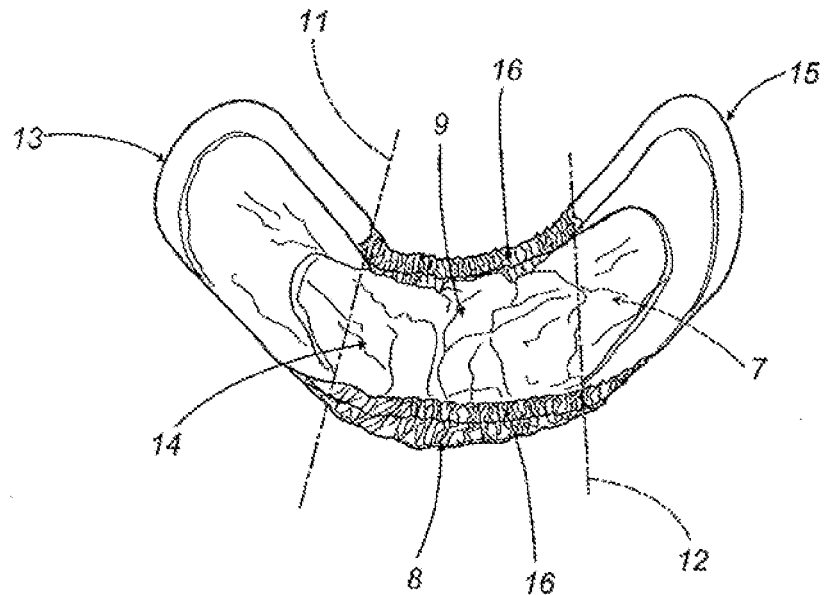

Also with reference to FIGS. 2 and 3, the incontinence pads 3 have a substantially rectangular shape, elongate according to a longitudinal axis A and comprise a central section of padding or absorbent pad 7.

The pad 7 is closed between a sheet of impermeable material (for example, polyethylene) which forms the outer face 8 of the incontinence pad 3, and a sheet of permeable material (for example non-woven fabric) which forms the inner face 9 of the incontinence pad 3.

Along the outline of the incontinence pad 3 the two sheets are sealed directly to each other, in such a way as to form a perimetric edge 10 with predetermined width.

As will be illustrated below, the folding unit 2 folds the incontinence pad 3, about fold lines 11 and 12 transversal to the axis A, into three portions having a substantially equal longitudinal dimension.

The three portion are hereinafter referred to respectively as the rear portion or first end portion 13, the central portion 14 and the front portion or second end portion 15 of the incontinence pad 3.

The two longitudinal sides of the edge 10, at least at their central zone 14, have an elasticated segment 16.

Therefore, the incontinence pad 3 comprises two elasticated segments 16 at the respective two substantially central portions of the longitudinal sides of the incontinence pad 3.

The presence of the elasticated segments 16 means that, when the packaging is opened, the incontinence pad 3, as shown in FIG. 3, adopts an anatomical shape.

The folding unit 2 comprises a conveyor for feeding the incontinence pads 3 according to the direction of the axis A.

In particular, the conveyor comprises a drum 17 which rotates continuously in the direction indicated by the arrow F, driven by motor means which are not illustrated, about an axis 18 which is at a right angle to the wall 4.

The numeral 19 denotes an infeed position for the incontinence pads 3, which are fed by a conveyor roller 20.

The conveyor roller 20 is part of the feed unit 5.

The numeral 21 denotes a position for outfeed and transfer of the folded incontinence pads 3 to the user unit 6.

Figure 4:
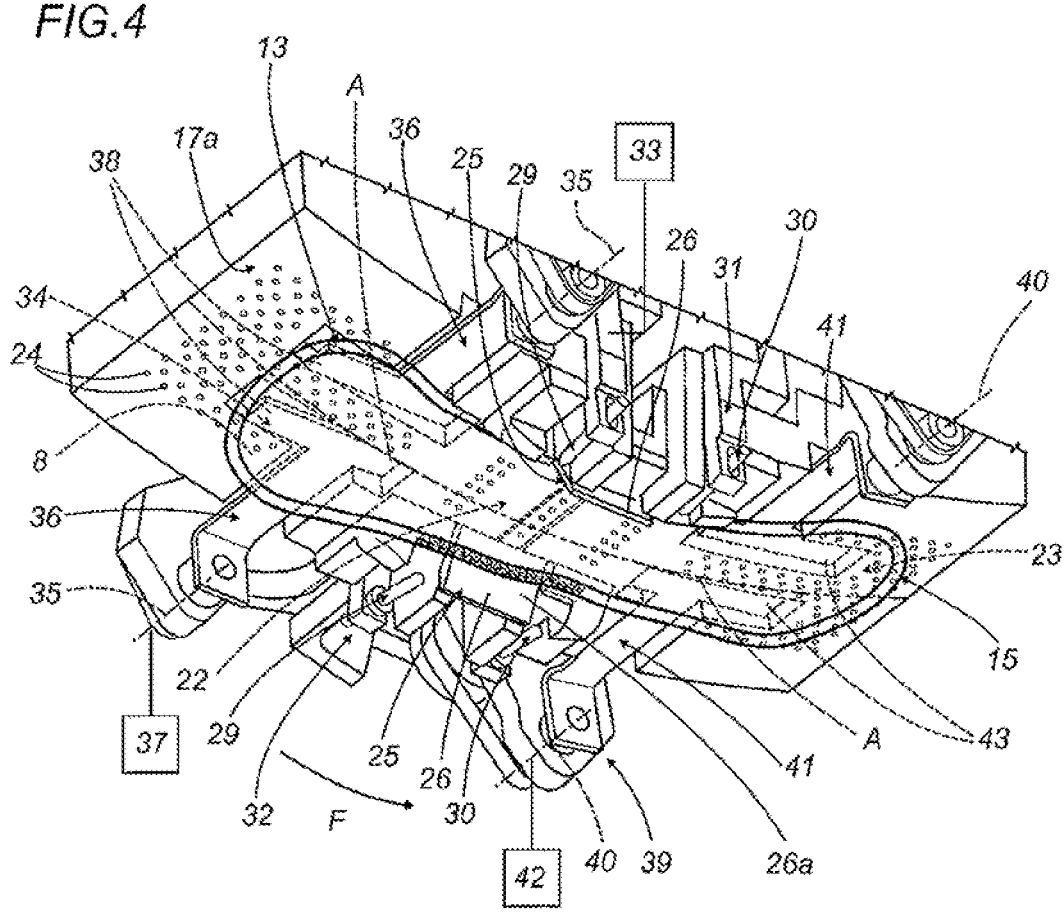
FIGS. 4, 5, 6 are perspective views of details of 1 in successive operating steps.
Figure 5:
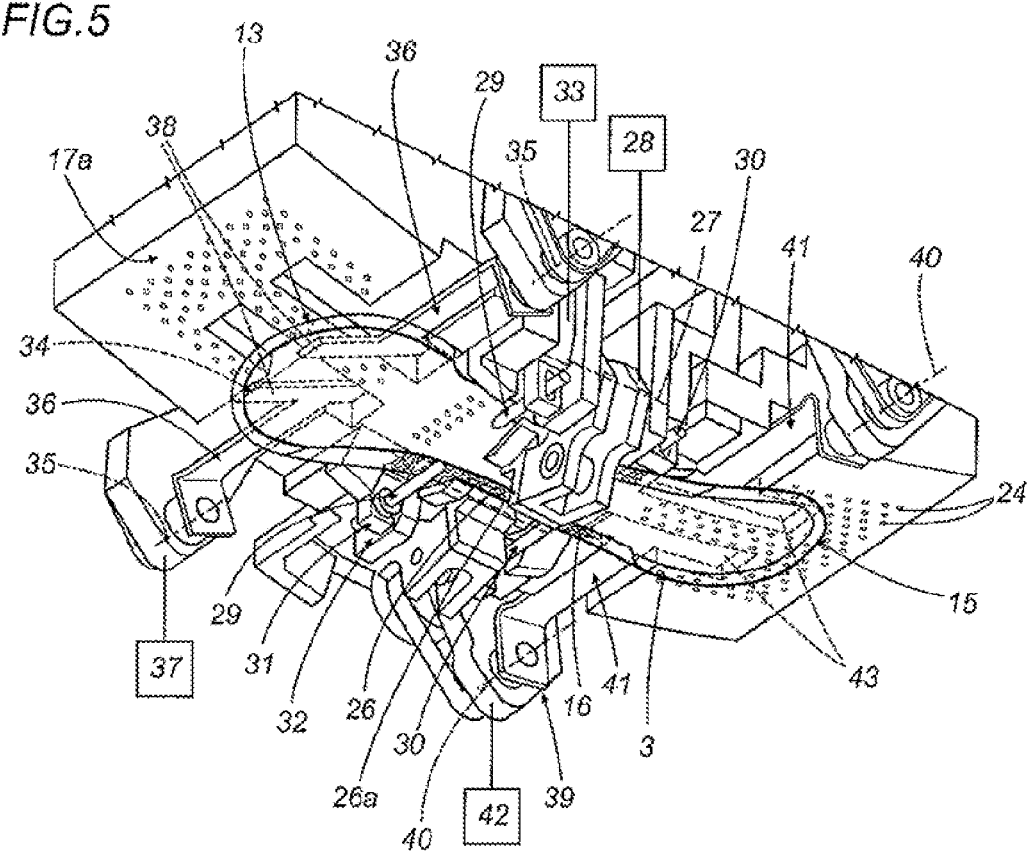
Figure 6:
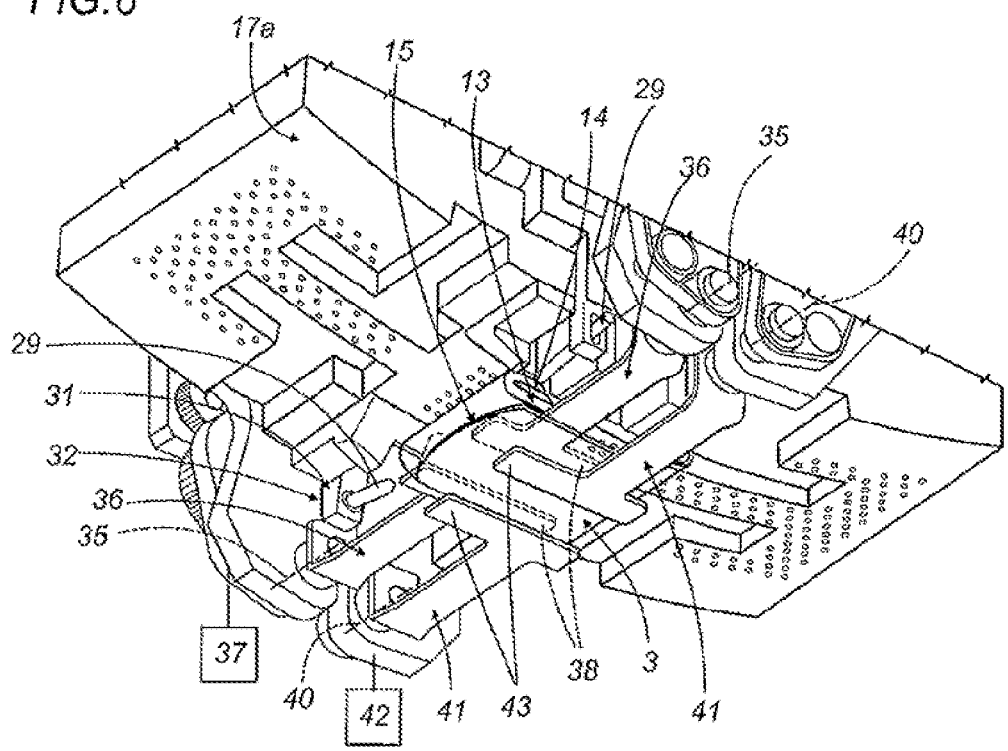

Also with reference to FIGS. 4, 5 and 6, the outer cylindrical surface, labelled 17a, of the drum 17 is divided into a plurality of suction cavities 22, spaced at equal angles to each other.

Each cavity 22 is designed to receive an incontinence pad 3 positioned with its axis A transversal to the axis 18, with its outer face 8 in contact with the cylindrical surface 17a and with the relative rear portion 13 positioned upstream with reference to the direction of rotation F of the drum 17.

The base, labelled 23, of each cavity 22 has a transversal dimension which is slightly greater than the transversal dimension of the absorbent pad 7 and is equipped with holes 24 connected to a suction source, not illustrated.

Associated with each cavity 22 there is a lateral folder 25 comprising two folding blades 26 which are positioned symmetrically relative to the cavity 22, at its intermediate zone, that is to say, at the zone relative to the central portion 14 of the incontinence pad 3.

Each folding blade 26 pivots at a respective axis 27 transversal to the axis 18 of the drum 17 and can move, driven by actuator means 28 with an oscillating movement.

The oscillating movement develops between a first position, disengaged relative to the cavity 22, and a second portion, inside the cavity 22, in which its free end, labelled 26a, is substantially in contact with the base 23 of the cavity 22.

Each folding blade 26 is inserted between the two prongs 29 and 30 of a fork-shaped element 31.

The prongs 29 and 30, parallel with the axis 18, are separated by a stretch substantially equal to that between the fold lines 11 and 12 of the incontinence pads 3.

The fork-shaped elements 31 can move, driven by actuator means 33, with an alternating motion between a disengaged position relative to the cavity 22, and an active position inside the cavity 22, substantially in contact with the base 23 of the cavity.

As described in more detail below, the fork-shaped elements 31 form means 32 for pressing and retaining the elasticated segments 16 on the central portion 14.

With reference in particular to FIG. 5, there is also a folder 34 associated with the upstream end of each cavity 22.

The folder 34 oscillates about an axis 35 which is parallel with the axis 18.

In particular, the folder 34 can move between a position, inside the drum 17, in which it is disengaged relative to the base 23 of the cavity 22, and a position inside the cavity 22 in which, in practice, it engages with the rear portion 13 of the incontinence pad 3.

The folder 34 comprises, positioned symmetrically relative to the cavity 22, two arms 36 which are coaxial relative to each other and parallel with the axis 18.

The two arms 36 are connected at one end to actuator means 37 and their free ends, labelled 38, are opposite each other and T-shaped.

There is also a folder 39 associated with the downstream end of each cavity 22, oscillating about an axis 40 which is parallel with the axis 18.

The folder 39 can move between a position, inside the drum 17, in which it is disengaged relative to the base 23 of the cavity 22, and a position inside the cavity 22 in which, in practice, it engages with the front portion 15 of the incontinence pad 3.

The folder 39 comprises, positioned symmetrically relative to the cavity 22, two arms 41 which are coaxial relative to each other and parallel with the axis 18. The two arms are connected at one end to actuator means 42 and their free ends, labelled 43, are opposite each other and T-shaped.

With reference also to FIG. 1, the numeral 44 denotes a guide wall coaxial with the drum 17 and forming, relative to the cylindrical surface 17a of the drum, a channel 45 whose size is approximately triple the thickness of the incontinence pad 3.

In practice, at the position 19 for infeed of the incontinence pads 3 they are transferred one after another from the conveyor roller 20 to the drum 17, which rotates continuously.

Each incontinence pad 3 is placed with the impermeable outer face 8 in contact with the base 23 of the respective cavity 22 and with the axis A angled transversally relative to the axis 18 of the drum 17.

It should be noticed that the adherence of the outer face 8 to the cylindrical surface 17a bends the incontinence pad 3 in the opposite direction to its definitive anatomical shape, thus tensioning the elasticated segments 16 and making them closely adhere to the base 23 of the cavity 22.

At a position 46 immediately downstream of the position 19, the two arms 36 of the folder 34, driven by the actuator means 37, perform a first rotation sub-step, clockwise when observing FIG. 5, their respective T-shaped ends 38 engaging with the rear portion 13.

Following that rotation the portion 13 detaches from the cylindrical surface 17a and is positioned at a predetermined angle (for example 120°) relative to the central portion, the result being that the tension in the two elasticated segments 16 is slackened.

During said first rotation sub-step, the arms 36 of the folder 34 consequently act as means for slackening the tension of the elasticated segments 16.

At a position 47, downstream of the position 46, the two blades 26 of the lateral folder 25 associated with the cavity 22 rotate, driven by the actuator 28, about the respective axes 27, in such a way as to engage with the two elasticated segments 16 and press them on the central portion 14.

That operation is performed substantially in such a way that it is synchronised with the action of the pressing and retaining device 32.

The prongs 29 and 30 of each fork-shaped element 31, when inserted in the cavity 22 on both sides of the blades 26, respectively form the fold lines 11 and 12 and at the same time hold the segments 16 in the folded position after the blades 26 have disengaged.

At a position 48 downstream of the position 47, the two arms 36 of the folder 34 perform a second and final rotation sub-step, pressing the rear portion 13 in contact with the central portion 14 of the incontinence pad 3.

At a position 49 downstream of the position 48, the two arms 41 of the folder 39, driven by the actuator means 42, perform an anti-clockwise rotation in such a way as to press the front portion 15 on the rear portion 13.

The incontinence pads 3 thus folded into three superposed portions are then inserted in the outfeed channel 45 and finally fed to the user unit 6.

From the above description it is clear how both the folding operation performed by the blades 26 and the insertion of the fork-shaped elements 31 are greatly facilitated by the previous partial folding of the rear portion 13, which results in slackening of the elasticated segments 16 and their loss of adherence relative to the base 23 of the cavity 22.

It is also obvious how the fork-shaped elements 31 perform the function of retaining means for the segments 16 on the central portion 14, define the fold lines 11 and 12 and act as guide means for the action of the folders 34 and 39.

Figure 7:
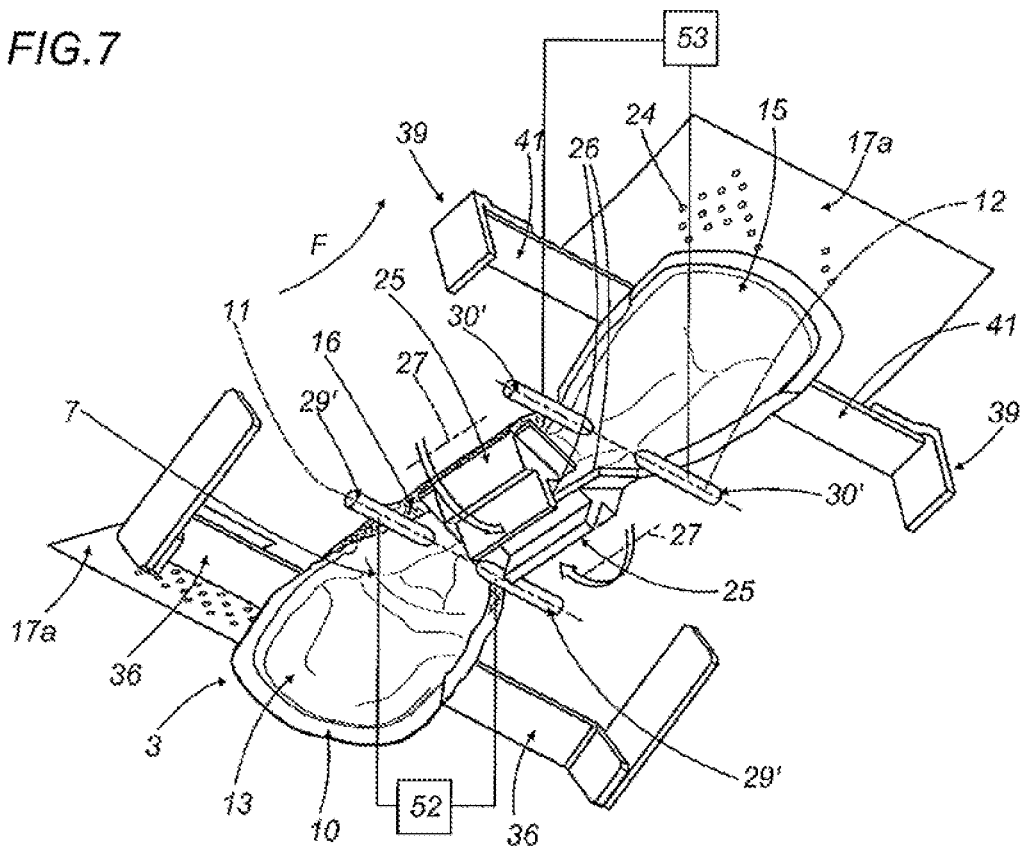
FIGS. 7 and 8 are perspective views of a second embodiment of details of 1 in successive operating steps.
Figure 8:
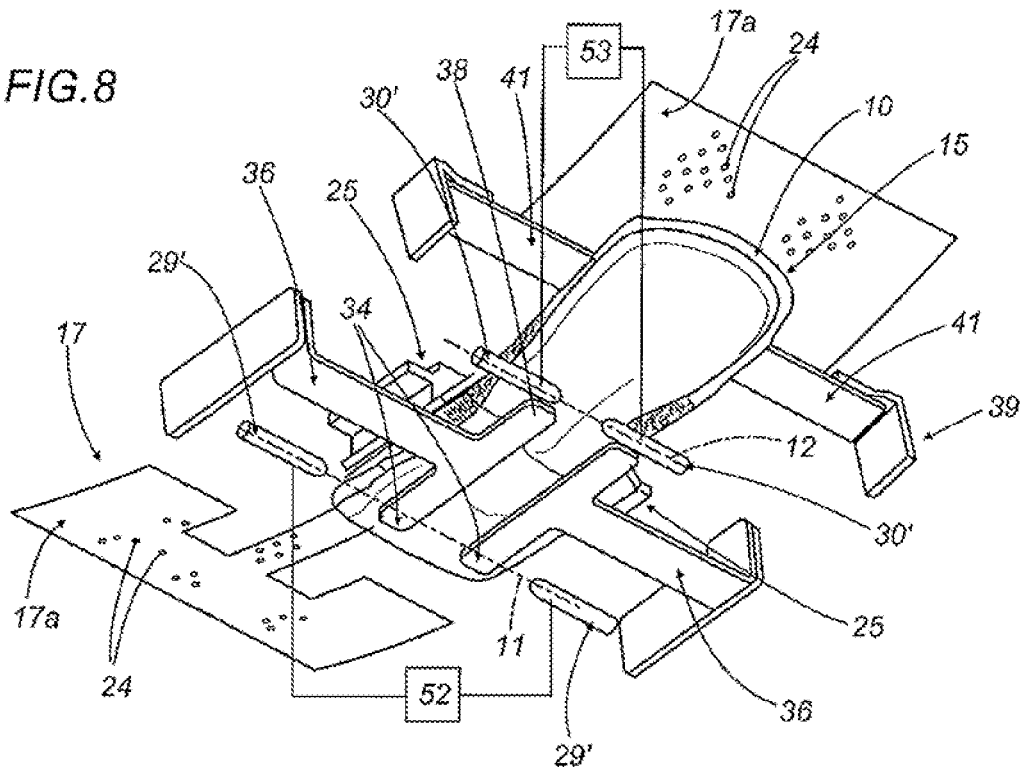

According to an alternative embodiment, shown in FIGS. 7 and 8, the two fork-shaped elements 31 of the pressing and retaining device 32 are substituted by two pairs of rods, respectively labelled 29' and 30'.

Driven by respective independent actuator means 52 and 53, the two pairs of rods 29' and 30' are simultaneously inserted in the cavity 22 at the fold lines 11 and 12 and are retracted from that position one after another, more precisely the pair of rods 29' after folding of the portion 13 and the pair of rods 30' after folding of the portion 15.

From the above description it is also possible to immediately infer the related method for folding incontinence pads according to this invention.

The invention claimed is:

1. A method for folding an incontinence pad, comprising:
   providing an incontinence pad having a substantially rectangular shape elongate according to a longitudinal axis and including a central absorbent pad and an outer edge,
   performing a first step of folding, about a first fold line transversal to the axis, a first end portion of the incontinence pad on a central portion of the incontinence pad, wherein, the first step of folding is performed by a first sub-step of beginning folding the first portion and a second sub-step of completely folding the first portion on the central portion,
   performing a second step of folding, about a second fold line transversal to the axis, a second end portion of the incontinence pad on the first end portion,
   performing a step of folding elasticated segments of the outer edge located between the first and second fold lines on the central portion;
   wherein the step of folding the elasticated segments of the outer edge begins between the first sub-step of beginning folding the first portion and the second sub-step of completely folding the first portion on the central portion;
   slackening a tension of the elasticated segments of the outer edge prior to the second sub-step of completely folding the first portion on the central portion.

2. The method for folding according to claim 1, wherein the step of folding the elasticated segments includes pressing and retaining the elasticated segments on the central portion.

3. The method for folding according to claim 2, wherein the pressing and retaining the elasticated segments comprises definition of the fold lines.

4. The method for folding according to claim 2, wherein the pressing and retaining the elasticated segments concludes at an end of the second step of folding.

5. The method for folding according to claim 2, wherein the pressing and retaining the elasticated segments concludes after the second step of folding.

6. The method for folding according to claim 1, wherein the slackening the tension of the elasticated segments of the outer edge is performed simultaneously with the first sub-step of beginning folding the first portion.

7. The method for folding according to claim 1, wherein the slackening the tension of the elasticated segments of the outer edge is performed by the first sub-step of beginning folding the first portion.

* * * * *